(12) United States Patent
Ravindranath et al.

(10) Patent No.: US 8,481,087 B2
(45) Date of Patent: Jul. 9, 2013

(54) WITHANIA SOMNIFERA PLANT EXTRACT AND METHOD OF PREPARATION THEREOF

(75) Inventors: Vijayalaksmi Ravindranath, Haryana (IN); Alok Gupta, Haryana (IN); Neha Sehgal, Haryana (IN); Subhash Chand Jain, Delhi (IN); Suman Thakur, Bangalore (IN); Pankaj Khanna, Delhi (IN)

(73) Assignees: National Brain Research Centre, Harayana (IN); Indian Institute of Science, Molecular Biophysics Unit, Bangalore (IN); University of Delhi, Department of Chemistry, New Delhi (IN)

( * ) Notice: Subject to any disclaimer, the term of this patent is extended or adjusted under 35 U.S.C. 154(b) by 38 days.

(21) Appl. No.: 13/003,758

(22) PCT Filed: Jul. 29, 2009

(86) PCT No.: PCT/IN2009/000430
§ 371 (c)(1),
(2), (4) Date: Jun. 6, 2011

(87) PCT Pub. No.: WO2010/013254
PCT Pub. Date: Feb. 4, 2010

(65) Prior Publication Data
US 2011/0229591 A1 Sep. 22, 2011

(30) Foreign Application Priority Data
Jul. 28, 2008 (IN) .......................... 1775/DEL/2008

(51) Int. Cl.
*A61K 36/00* (2006.01)
(52) U.S. Cl.
USPC .......................................... 424/725; 424/773

(58) Field of Classification Search
None
See application file for complete search history.

(56) References Cited

U.S. PATENT DOCUMENTS
2004/0258781 A1* 12/2004 Nair et al. ..................... 424/769

FOREIGN PATENT DOCUMENTS
WO WO 2005/034846 A2 4/2005

OTHER PUBLICATIONS

Tohda et al, Scientific basis for the anti-dementia drugs of constituents from Ashwagandha (*Withania somnifera*). Journal of Traditional Medicines (2005) vol. 22, No. Suppl.1, pp. 176-182.*
Kuboyama, T., et al., "Withanoside IV and its active metabolite, sominone, attenuate Aβ(25-35)-induced neurodegeneration," *European Journal of Neuroscience*, vol. 23(6), pp. 1417-1426 (2006).
Kulkarni, S., et al., "*Withania somnifera*: An Indian ginseng," *Progress in Neuro-Psychopharmacology & Biological Psychiatry*, vol. 32(5), pp. 1093-1105 (2008).
Sankar, S., et al,. "The Neuroprotective Effect of *Withania somnifera* Root Extract in MPTP-Intoxicated Mice: An Analysis of Behavioral and Biochemical Varibles," *Cellular & Molecular Biology Letters*, vol. 12(4), pp. 473-481 (2007).
Richardson et al., "Mouse Models of Alzheimer's Disease: A Quest for Plaques and Tangles," ILAR Journal, vol. 43, No. 2 (2002), pp. 89-99.

* cited by examiner

*Primary Examiner* — Qiuwen Mi
(74) *Attorney, Agent, or Firm* — Kilpatrick Townsend & Stockton LLP

(57) ABSTRACT

The present invention provides *Withania somnifera* plant extract and composition comprising the extract useful for the treatment of neurodegenerative disease and/or disorders such as Alzheimers disease (AD). The present invention further provides a process for preparation of the extract.

9 Claims, 7 Drawing Sheets

Cortical Beta Amyloid in 9 months male mice

Beta Amyloid in 23 months female mice

WITHANIA SOMNIFERA PLANT EXTRACT AND METHOD OF PREPARATION THEREOF

CROSS-REFERENCE TO RELATED APPLICATIONS

The present application is a U.S. National Stage Application of PCT/IN2009/000430, filed Jul. 29, 2009, which claims the benefit of Indian Application No. 1775/DEL/2008, filed Jul. 28, 2008, the entire disclosure disclosures of which are hereby incorporated herein by reference.

FIELD OF INVENTION

The present invention relates to *Withania somnifera* plant extract compositions and its use in treatment for neurodegenerative diseases or disorders such as Alzheimer's disease (AD).

BACKGROUND OF THE INVENTION

The incidence of various neurodegenerative disorders such as Alzheimer's disease (AD), Parkinson's disease (PD) and senile dementia increases with age. While PD is characterized by tremors, rigidity and bradykinesia, AD is characterized by short term memory loss followed by cognitive (intellectual) impairment affecting higher cognitive functions such as domains of language, skilled movements and recognition causing aphasia, apraxia and agnosia respectively. It also affects functions such as decision-making and planning closely related to the frontal and temporal lobes of the brain.

Epidemiology of Alzheimer's disease indicates that more than 26 million people worldwide were affected with Alzheimer's disease in 2006 and the number will increase to more than 106 million by 2050 (Brookmeyer R, Johnson E, Ziegler-Graham K, Arrighi H M, "Forecasting the Global Burden of Alzheimer's Disease. Alzheimer's and Dementia," 3:186-191(2007). The greatest increase in prevalence of AD will occur in Asia, where 48 percent of the world's Alzheimer's cases currently reside. The number of cases is expected to grow in Asia from 12.65 million in 2006 to 62.85 million in 2050.

Alzheimer's disease is a progressive and irreversible neurodegenerative disorder, and currently no cure is available since the etiopathogenesis of this disorder is poorly understood. The marketed drugs available for AD do not prevent or reverse this disease and are approved only for the management of the symptoms (Melnikova, 2007). Early detection and therapeutic interventions are urgently needed to minimize the ill effects of this devastating disease. Traditional systems of medicine such as Ayurveda offer an extensive resource, which can be utilized for development of therapeutic intervention strategies for treatment of these disorders.

Currently plant species are extensively used for medicinal purposes. Herbs are natural and safer than synthetic drugs and they are effective in treating many complex disorders of the nervous system. For instance, *Ginkgo biloba* extract has been shown to block impairment in spatial learning and memory in a mouse model of AD (Quinn et. al. 2003). Similarly, past studies have shown that ashwagandha can help boost memory.

*Withania somnifera* (Ashwagandha) traditionally also known as Indian ginseng is one of the major herbal components of geriatric tonics mentioned in Indian systems of medicine. Ashwagandha is known for treatment and prevention of a diverse range of ailments. The traditional uses of the herb are as a tonic and invigorator. It is believed to prolong longevity, boost mental and physical stamina, and improve sexual function (which is how it earned the nickname herbal viagra). It also helps to improve learning ability and memory capacity.

Withanolide-A, one of the component of the plant extract had been shown to regenerate neurites and reconstruct synapses in severely damaged neurons in vitro (Kuboyama T, Tohda C, Komatsu K, "Neuritic regeneration and synaptic reconstruction induced by withanolide A," Br J Pharmacol. 2005 April; 144(7):961-71).

Ghoshal (U.S. Pat. No. 6,713,092, 2004) discloses a process of preparation of *Withania somnifera* extract from root and leaves of 1-2 years old plant. The process comprises aqueous-alcoholic extraction in the presence of exogenous polysaccharides.

Ghoshal (U.S. Pat. No. 7,318,938, 2008) discloses *Withania somnifera* extract composition in the form of a stable herbaceous powder which provides enhanced cognition enhancing effects for the user. The composition comprises 8-25% of withanolide glycosides and sitoindosides, 25-75% oiligosaccharides, polysaccharide (less than 10%) and free withaferrin A (less than 2%).

SUMMARY OF THE INVENTION

The present invention provides *Withania somnifera* plant extract composition and a process for preparation of the extract. The plant extract disclosed in the present invention is useful for the treatment of neurodegenerative diseases or disorders such as Alzheimer's disease.

One aspect of the present invention provides a *Withania somnifera* extract comprising about 70-80% withanolides and about 15-25% withanoside.

One aspect of the present invention provides a *Withania somnifera* extract comprising 75% withanolides and 20% withanoside.

Another aspect of the present invention provides a pharmaceutical composition comprising the *Withania somnifera* extract comprising about 75% withanolides and about 20% withanoside and a pharmaceutical acceptable carrier.

Another embodiment of the present invention provides a nutritional composition comprising the *Withania somnifera* extract comprising about 75% withanolides and about 20% withanoside.

Yet another aspect of the present invention provides an herbal composition comprising the *Withania somnifera* extract comprising about 75% withanolides and about 20% withanoside.

Still yet another aspect of the present invention provides a process for preparation of *Withania somnifera* plant extract, the process comprises providing *Withania* roots, extracting said roots with organic solvent at a room temperature for about 60-75 hours to obtain root extract; removing the solvent from the root extract to obtain dry root extract; treating the dry root extract with 10% methanol-chloroform mixture to obtain active fraction of the root extract.

Still yet another aspect of the present invention provides use of the *Withania somnifera* extracts comprising about 75% withanolides and about 20% withanoside for preparation of medicament useful for the treatment of neurodegenerative disorders is selected from a group consisting of Alzheimer's disease (AD), Parkinson's disease (PD) and senile dementia.

Yet another aspect of the present invention provides a method of ameliorating neurodegenerative disorders comprising administering to a subject in need thereof a therapeutically effective amount of the *Withania somnifera* plant extract comprising about 75% withanolides and about 20% withanoside.

BRIEF DESCRIPTION OF THE ACCOMPANYING DRAWING

(a) Coronal Brain Sections were cut serially and stained (every $10^{th}$) for plaques using Bielschowsky's Silver staining and immunostained for β-amyloid and Ubiquitin (Ubiquitin-IHC).

(b) Quantitative assessment of the percentage surface area covered by plaques, immunostained by amyloid and ubiquitinated protein aggregates in cortex and hippocampus is depicted. All Data are mean±S.D (n=4). Asterisks indicate values significantly different from controls (p<0.001). Treatment groups are represented as vehicle treated (V/Veh), plant extract treated (T/Trt) and images are taken from cortex (CT), hippocampus (HP).

Figure 3:
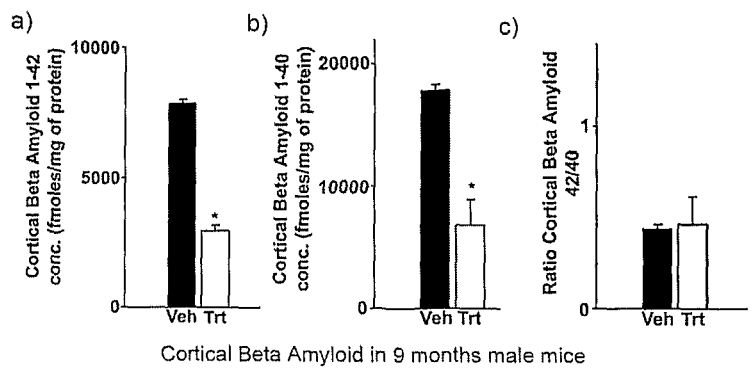

FIG. 3 shows *Withania somnifera* plant extract (1 g/kg body weight) reduces β-amyloid burden in cortex of 9 months old Tg male mice. Amyloid burden was quantified using ELISA for Aβ (1-42;a), Aβ (1-40; b) and c depicts the ratio between Aβ42 & Aβ40. Data are mean±S.D (n=6). Asterisks indicate values significantly different from controls (p<0.001).

Figure 4:
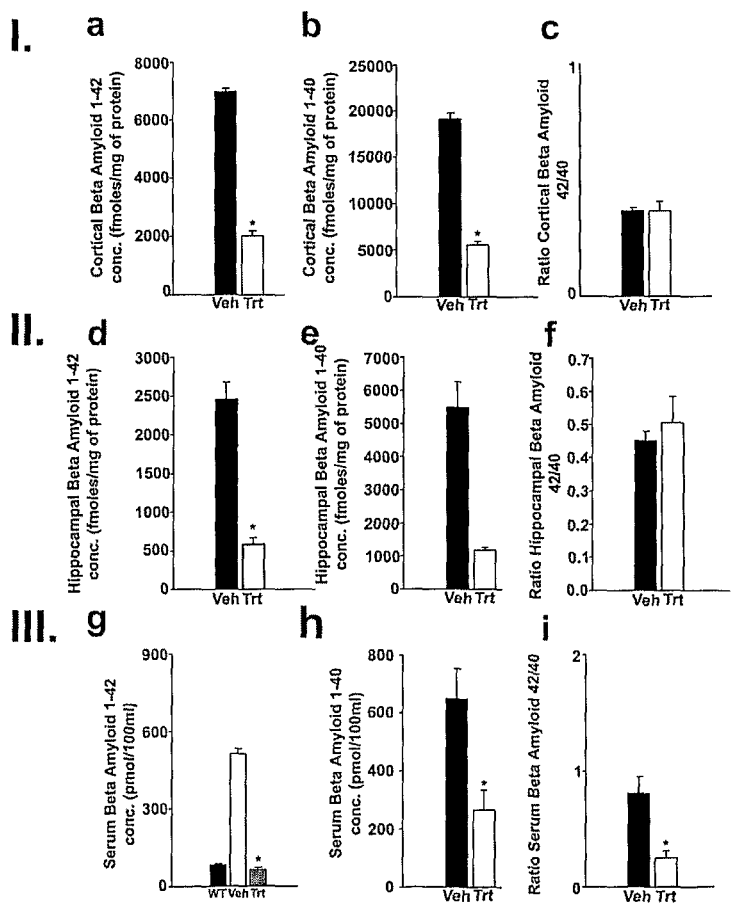

FIG. 4 shows *Withania somnifera* plant extract (1 g/kg) reduces β-amyloid burden in 9 months old Tg female mice. Amyloid burden was quantified using ELISA. Panel I, II, III depicts the Aβ load in cortex, hippocampus and serum respectively. a, d, g represents quantification of Aβ (1-42); b, e, h represents quantification Aβ (1-40) and c, f, i depicts the ratio of Aβ42 and Aβ40. All data are mean±S.D. (n=5). Asterisks indicate values significantly different from controls (p<0.001).

Figure 5:
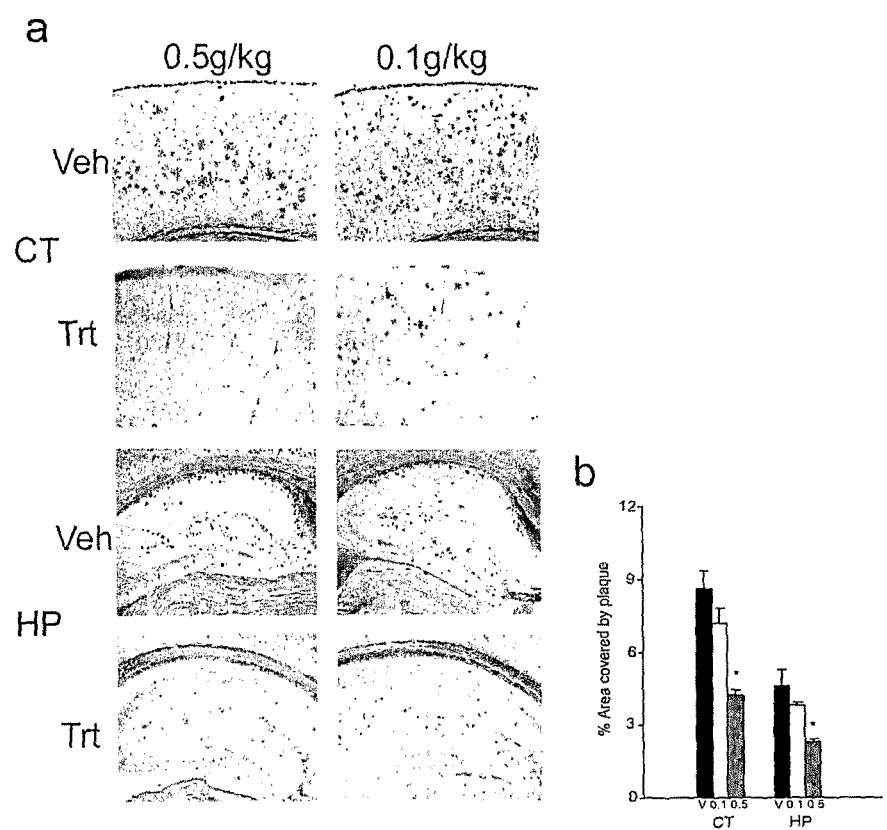

FIG. 5 shows reduction in plaques and ubiquitinated protein aggregates in Tg mice (9 months old) on treatment with *Withania somnifera* plant extract (dose: 0.1 gm/kg & 0.5 gm/kg). (a) Coronal Brain Sections were cut serially and stained (every $10^{th}$ day) for plaques using Bielschowsky's Silver staining. (b) Quantitative assessment of the percentage surface area covered by plaques in cortex and hippocampus is depicted. All Data are mean±S.D (n=5). Asterisks indicate values significantly different from controls (p<0.001). The Group animals are represented as vehicle treated (V/Veh), plant extract treated (T/Trt) and images are taken from cortex (CT), hippocampus (HP).

Figure 6:
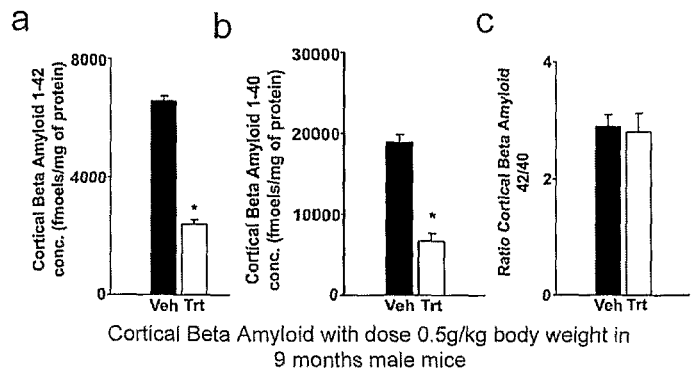

FIG. 6 shows reduction in β-amyloid burden in cortex of 9 months old Tg male mice on treatment with *Withania somnifera* plant extract (0.5 g/kg). ELISA is done to quantify (a) Aβ (1-42), (b) Aβ (1-40) and (c) depicts the ratio between Aβ42 & Aβ40. Data are mean±S.D (n=6). Asterisks indicate values significantly different from controls (p<0.001).

Figure 7:
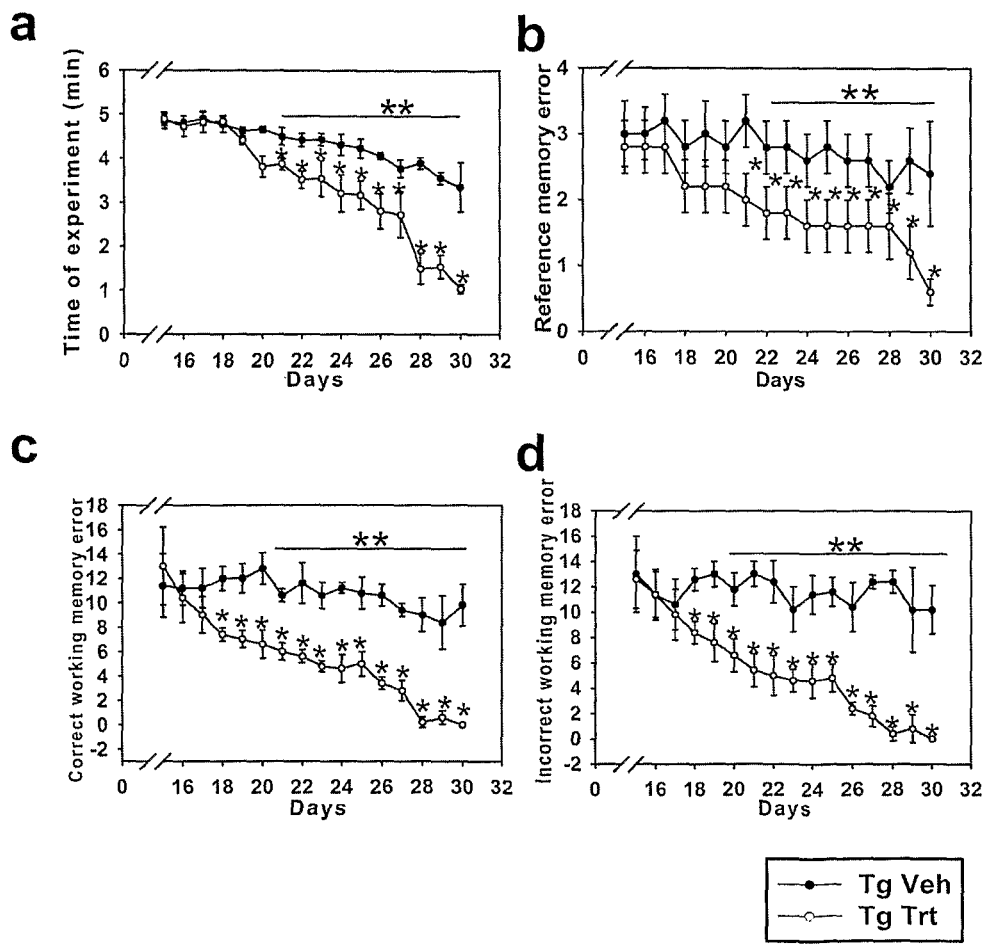

FIG. 7 shows improvement in the learning and memory performance of 23 month old Tg mice after treatment with *Withania somnifera* plant extract (PE) by testing on radial arm maze (RAM). Female APP/PS1 mice (23 months-old) were treated with PE (1 g/kg), vehicle for a total period of 30 days during which their performance on the RAM was assessed. (a) Time of experiment is assessed as the time to complete the task (b) Reference memory error (RME) is assessed as number of first entries into unbaited arm. (c) Correct working memory error (CWE) is assessed as number of reentries into baited arm. (d) Incorrect working memory error (ICWE) is assessed as number of reentries into unbaited arm. Data are mean±S.D (n=5). Asterisks indicate values significantly different from controls (p<0.001). The group animals are represented as vehicle treated transgenic (Tg-Veh); plant extract treated transgenic (Tg-Trt).

Figure 8:
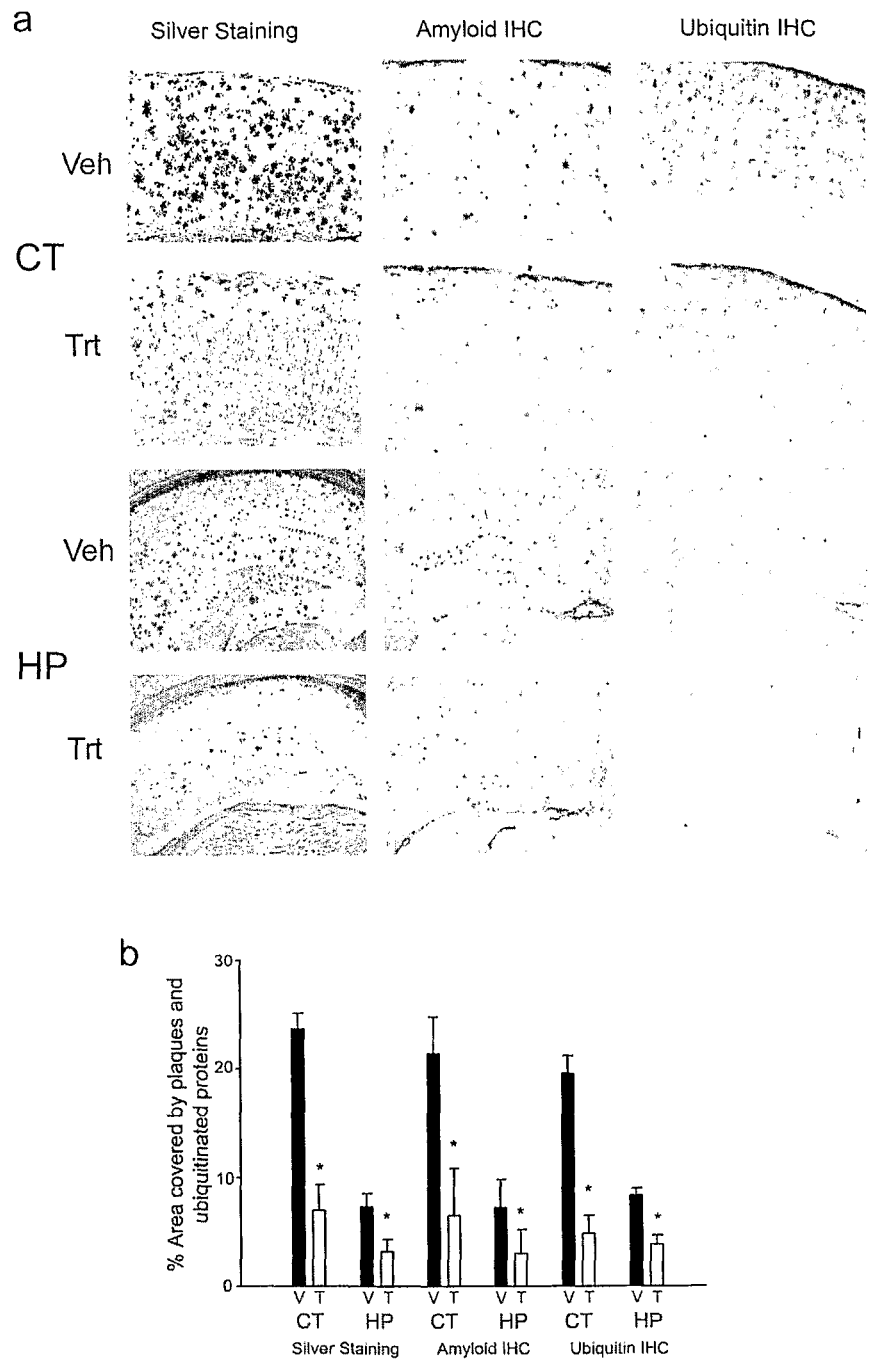

FIG. 8 shows reduction in plaques and ubiquitinated protein aggregates in 23 months old Tg mice on treatment with plant extract (dose: 1 gm/kg body weight). (a) Coronal Brain Sections were cut serially and stained (every $10^{th}$ day) for plaques using Bielschowsky's Silver staining and immunostained for β-amyloid and Ubiquitin (Ubiquitin-IHC). (b) Quantitative assessment of the percentage surface area covered by plaques, immunostained by amyloid and ubiquitinated protein aggregates in cortex and hippocampus is depicted. All Data are mean±S.D (n=5). Asterisks indicate values significantly different from controls (p<0.001). Treatment groups are represented as vehicle treated (V/Veh), plant extract treated (T/Trt) and images are taken from cortex (CT), hippocampus (HP).

Figure 9:
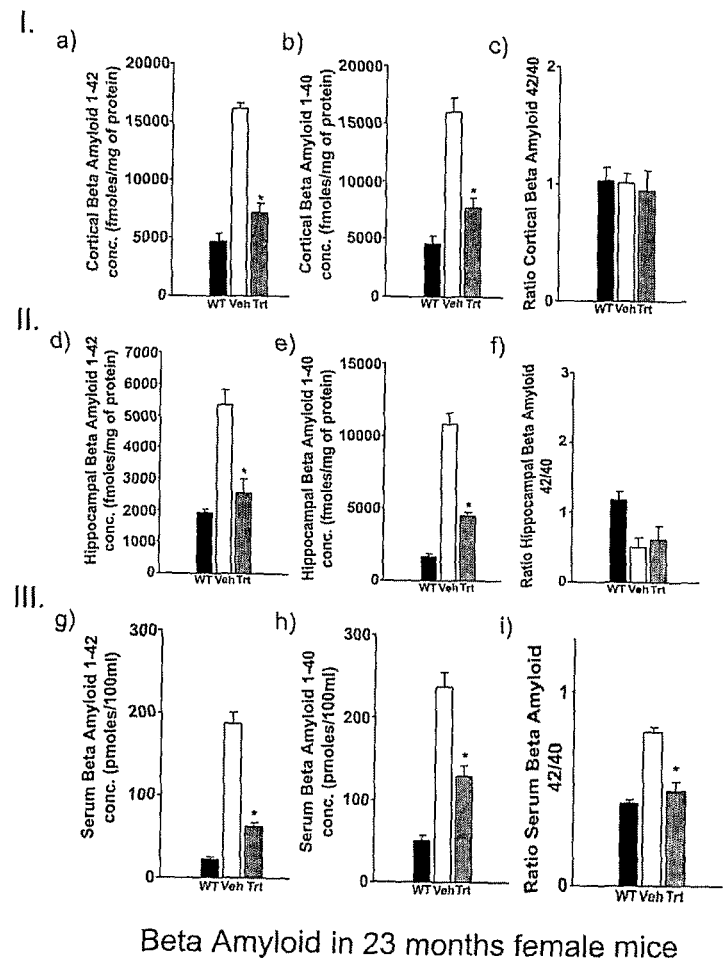

FIG. 9 shows reduction in β-amyloid burden in 23 months old Tg female mice on treatment with *Withania somnifera* plant extract (1 g/kg). Amyloid burden was quantified using ELISA. Panel I, II, III depicts the Aβ load in cortex, hippocampus and serum respectively. a, d, g represents quantification of Aβ (1-42); b, e, h represents quantification Aβ (1-40) and c, f, i depicts the ratio of Aβ42 and Aβ40. All data are mean±S.D. (n=5). Asterisks indicate values significantly different from controls (p<0.001).

DETAILED DESCRIPTION OF THE INVENTION

As used herein, the terms '*Withania somnifera* extract', *Withania* root extract', 'root extract', 'plant extract' and 'herb extract' may be used interchangeably.

The present invention provides *Withania somnifera* plant extract composition and its use in treatment for neurodegenerative diseases or disorders such as Alzheimer's disease. The invention further provides a process for preparing the extract.

Further, the present invention provides a method for preparation of plant extract from *Withania somnifera* roots, which comprises preparing dried *Withania* root powder by conventional methods, adding CHCl$_3$/MeOH (1:1) to root powder; stirring at room temperature for about 72 hours; filtering the contents and removing the solvent from the clear filtrate under reduced pressure using rotavapor at 35-40° C.; adding fresh CHCl$_3$/MeOH (1:1) to the extracted plant material and repeating the extraction procedure four times, checking the extracts for homogeneity removing the solvent from the combined extract and removing the traces of solvent by air-drying at room temperature to obtain purified plant extract comprising the biologically active ingredient of *Withania somnifera* roots.

The present invention relates to *Withania somnifera* plant extract and compositions comprising biologically active ingredient of *Withania somnifera* extract such as root extract.

The present invention relates to *Withania somnifera* extract and a pharmaceutical composition comprising biologically active ingredient of *Withania somnifera* extract.

One aspect of the present invention provides use of *Withania somnifera* extract in prophylactic and therapeutic treatment of neurological diseases.

One aspect of the present invention provides use of *Withania somnifera* extract in prophylactic and therapeutic treatment of neurodegenerative disorders.

Another aspect of the present invention provides use of *Withania somnifera* extract in prophylactic and therapeutic treatment of Alzheimer's disease.

Yet, another aspect of the present invention provides a pharmaceutical composition comprising biologically active ingredient of *Withania somnifera* extract useful for prophylactic and therapeutic treatment of neurological diseases.

Yet, another aspect of the present invention provides a pharmaceutical composition comprising biologically active ingredient of *Withania somnifera* extract useful for prophylactic and therapeutic treatment of neurodegenerative disorders.

Yet, another aspect of the present invention provides a pharmaceutical composition comprising biologically active ingredient of *Withania somnifera* extract useful for therapeutic and prophylactic treatment of Alzheimer's disease.

One aspect of the present invention provides use of *Withania somnifera* extract in the manufacture of medicament for the prophylactic and therapeutic treatment of neurological diseases.

One aspect of the present invention provides use of *Withania somnifera* extract in the manufacture of medicament for the prophylactic and therapeutic treatment of neurodegenerative diseases.

Another aspect of the present invention provides use of *Withania somnifera* extract in the manufacture of medicament for the prophylactic and therapeutic treatment of Alzheimer's disease.

Another aspect of present invention provides a therapeutic method of treatment of neurological disorders comprising providing effective amount of pharmaceutical composition having biologically active ingredient of *Withania* root.

Another aspect of present invention provides a therapeutic method of treatment of neurodegenerative disorders comprising providing effective amount of pharmaceutical composition having biologically active ingredient of *Withania* root.

Another aspect of present invention provides a therapeutic method of treatment of Alzheimer's disease comprising providing effective amount of pharmaceutical composition having biologically active ingredient of *Withania* root.

Yet another aspect of present invention provides a prophylactic method of treatment of neurological disorders comprising providing effective amount of pharmaceutical composition having biologically active ingredient of *Withania* root.

Yet another aspect of present invention provides a prophylactic method of treatment of neurodegenerative disorders comprising providing effective amount of pharmaceutical composition having biologically active ingredient of *Withania* root.

Another aspect of present invention provides a prophylactic method of treatment of Alzheimer's disease comprising providing effective amount of pharmaceutical composition having biologically active ingredient of *Withania* root.

The present invention relates to *Withania somnifera* extract and compositions comprising biologically active ingredient of *Withania somnifera* extract.

One embodiment of the present invention provides use of biologically active ingredient of *Withania somnifera* extract in prophylactic and therapeutic treatment of diseases.

Another embodiment of the present invention provides use of *Withania somnifera* extract in prophylactic and therapeutic treatment neurological diseases or disorders.

Another embodiment of the present invention provides use of *Withania somnifera* extract in prophylactic and therapeutic treatment neurodegenerative diseases or disorders.

Yet, another embodiment of the present invention provides use of *Withania somnifera* extract in prophylactic and therapeutic treatment of Alzheimer's disease.

One embodiment of the present invention provides the use of *Withania* root extract as a health or nutritional supplement.

One embodiment of the present invention provides a pharmaceutical composition comprising biologically active ingredient of *Withania somnifera* extract useful for therapeutic and/or prophylactic treatment of neurological diseases.

One embodiment of the present invention provides a pharmaceutical composition that can be administered in combination with other pharmaceutical drugs and/or compositions for treatment of diseases.

Another embodiment of the present invention provides a composition comprising an effective amount of *Withania somnifera* extract along with pharmaceutically acceptable excipients.

Another embodiment of the present invention provides use of composition comprising an effective amount of *Withania somnifera* extract along with pharmaceutically acceptable excipients as a health or nutritional supplement.

Another embodiment of the present invention is the use of *Withania somnifera* extract in the manufacture of medicament for the therapeutic and/or prophylactic treatment of neurological diseases or disorders.

Another embodiment of the present invention is the use of *Withania somnifera* extract in the manufacture of medicament for the therapeutic and/or prophylactic treatment of neurodegenerative diseases or disorders.

Another embodiment of the present invention is the use of *Withania somnifera* extract in the manufacture of medicament for the therapeutic and/or prophylactic treatment of Alzheimer's disease.

The extraction can be carried out by the general extraction methods such as alcohol digestion, steam distillation, supercritical fluid extraction method by adding co-solvent and other conventional methods of extraction.

The present invention provides a therapeutic method of treatment of neurological disorders comprising providing effective amount of pharmaceutical composition having biologically active ingredient of *Withania* root.

The present invention further provides a prophylactic method of treatment of neurological disorders comprising providing effective amount of pharmaceutical composition having biologically active ingredient of *Withania* root.

One embodiment of the present invention provides a method for preparation and purification of plant extract from *Withania somnifera* roots, which comprises the steps of preparing dried *Withania* root powder by conventional methods, adding $CHCl_3$/MeOH (1:1) to root powder; stirring at room temperature for about 72 hours; filtering the contents and removing the solvent from the clear filtrate under reduced pressure using rotavapor at 35-40° C.; adding fresh $CHCl_3$/MeOH (1:1) to the extracted plant material and repeating the extraction procedure four times; checking the extracts for homogeneity removing the solvent from the combined extract and removing the traces of solvent by air-drying at room temperature to obtain purified plant extract comprising the biologically active ingredient of *Withania* root.

Figure 1:
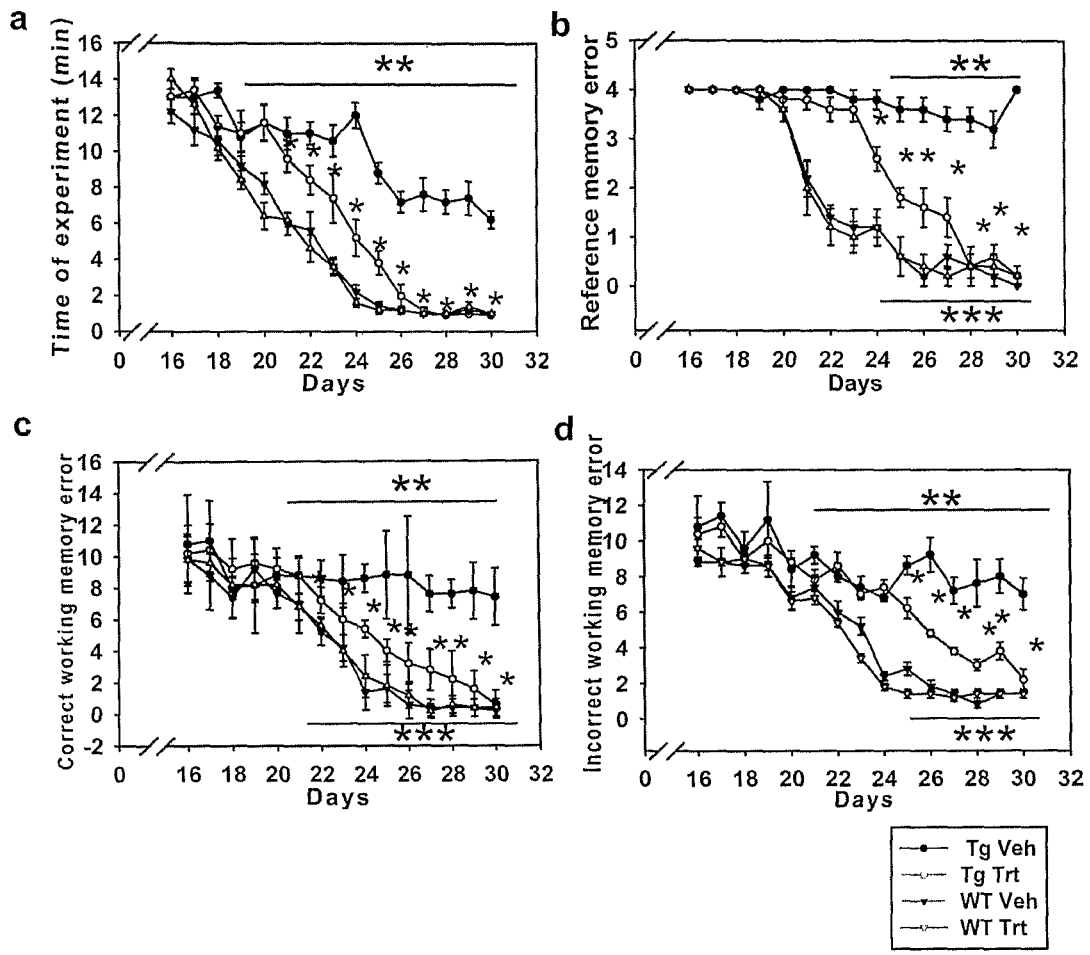
FIG. 1 shows that plant extract (PE) treatment improves the learning and memory performance of Tg mice in radial arm maze (RAM)

FIG. 1: Male APP/PS1 mice (9 months-old) were treated with PE (1 g/kg) or vehicle for a total period of 30 days during which their performance on the RAM was assessed. (a) Time of experiment is assessed as the time to complete the task (b) Reference memory error (RME) is assessed as number of first entries into unbaited arm. (c) Correct working memory error (CWE) is assessed as number of reentries into baited arm. (d) Incorrect working memory error (ICWE) is assessed as number of reentries into unbaited arm. WT-Veh and WT-Trt performed similarly in RAM for all the parameters. Data is represented as mean±SD (n=6). Asterisks indicate values significantly different from controls (p<0.05). Treatment groups are represented as vehicle treated transgenic (Tg-Veh); plant extract treated transgenic (Tg-Trt); vehicle treated wild type (WT-Veh) and plant extract treated wild type (WT-Trt).

In accordance with the present invention in one embodiment there is provided a *Withania somnifera* extract comprising about 70-80% withanolides and about 15-25% withanoside.

In accordance with the present invention in one embodiment there is provided a *Withania somnifera* extract comprising 75% withanolides and 20% withanoside.

In yet another embodiment of the present invention there is provided the *Withania somnifera* extract comprising about 75% withanolides and about 20% withanoside, wherein the extract is free of withaferrin.

In yet another embodiment of the present invention there is provided The *Withania somnifera* extract the *Withania somnifera* extract comprising about 75% withanolides and about 20% withanoside, wherein the extract is obtained from roots of *Withania somnifera*.

One embodiment of the present invention provides the *Withania somnifera* extract comprising about 75% withanolides and about 20% withanoside, wherein the extract is useful for the treatment of neurodegenerative disorders is selected from a group consisting of Alzheimer's disease, Parkinson's disease and senile dementia.

Another embodiment of the present invention provides the *Withania somnifera* extract comprising about 75% withanolides and about 20% withanoside, wherein the extract is in the form of powder, liquid, capsules or tablets.

Another embodiment of the present invention provides the *Withania somnifera* extract comprising about 75% withanolides and about 20% withanoside, wherein the extract is useful for the treatment of Alzheimer's disease.

Another embodiment of the present invention provides the *Withania somnifera* extract comprising about 75% withanolides and about 20% withanoside, wherein the extract is useful for the treatment of Alzheimer's disease, wherein effective dosage of the extract for the treatment of Alzheimer's disease is in the range of 0.5 g/day/kg body weight to 1 g/day/kg body weight.

In another embodiment of the present invention there is provided a pharmaceutical composition comprising the *Withania somnifera* extract comprising about 70-80% withanolides and about 15-25% withanoside and a pharmaceutical acceptable carrier.

There is provided a nutritional composition comprising the *Withania somnifera* extract comprising about 70-80% withanolides and about 15-25% withanoside.

The present invention further provides an herbal composition comprising the *Withania somnifera* comprising about 70-80% withanolides and about 15-25% withanoside.

In one embodiment of the present invention there is provided a process for preparation of *Withania somnifera* plant extract, the process comprises providing *Withania* roots, extracting said roots with organic solvent at a room temperature for about 60-75 hours to obtain root extract; removing the solvent from the root extract to obtain dry root extract; treating the dry root extract with 10% methanol-chloroform mixture to obtain active fraction of the root extract.

In one embodiment of the present invention there is provided a process for preparation of *Withania somnifera* plant extract, the process comprises providing *Withania* roots, extracting said roots with organic solvent at a room temperature for about 60-75 hours to obtain root extract; removing the solvent from the root extract to obtain dry root extract; treating the dry root extract with 10% methanol-chloroform mixture to obtain active fraction of the root extract, wherein organic solvent is a mixture of chloroform and Methanol.

In one embodiment of the present invention there is provided a process for preparation of *Withania somnifera* plant extract, the process comprises providing *Withania* roots, extracting said roots with organic solvent at a room temperature for about 60-75 hours to obtain root extract; removing the solvent from the root extract to obtain dry root extract; treating the dry root extract with 10% methanol-chloroform mixture to obtain active fraction of the root extract, wherein organic solvent is a mixture of chloroform and Methanol, wherein ratio of chloroform to methanol is 2:3, 1:1 or 3:2.

In one embodiment of the present invention there is provided a process for preparation of *Withania somnifera* plant extract, the process comprises providing *Withania* roots, extracting said roots with organic solvent at a room temperature for about 60-75 hours to obtain root extract; removing the solvent from the root extract to obtain dry root extract; treating the dry root extract with 10% methanol-chloroform mixture to obtain active fraction of the root extract, wherein organic solvent is a mixture of chloroform and Methanol, wherein ratio of chloroform to methanol is 1:1.

In another embodiment of the present invention there is provided a method of ameliorating neurodegenerative disorders comprising administering to a subject in need thereof a therapeutically effective amount of the *Withania somnifera* plant extract comprising about 70-80% withanolides and about 15-25% withanoside.

In another embodiment of the present invention there is provided a method of ameliorating neurodegenerative disorders comprising administering to a subject in need thereof a therapeutically effective amount of the *Withania somnifera* plant extract comprising 75% withanolides and 20% withanoside.

Another embodiment of the present invention provides a method of ameliorating neurodegenerative disorders comprising administering to a subject a therapeutically effective amount of the *Withania somnifera* plant extract comprising about 70-80% withanolides and about 15-25% withanoside, wherein the neurodegenerative disorders is selected from a group consisting of Alzheimer's disease, Parkinson's disease and senile dementia.

Another embodiment of the present invention provides a method of ameliorating neurodegenerative disorders comprising administering to a subject in need thereof a therapeutically effective amount of the *Withania somnifera* plant extract comprising about 70-80% withanolides and about 15-25% withanoside, wherein the neurodegenerative disorders is Alzheimer's disease.

Another embodiment of the present invention provides a method of ameliorating neurodegenerative disorders comprising administering to a subject in need thereof a therapeutically effective amount of the *Withania somnifera* plant extract comprising about 70-80% withanolides and about 15-25% withanoside, wherein the *Withania somnifera* plant extract is administered to a subject at a dose of about 0.5 g/day/kg body weight to 1 g/day/kg body weight.

In another embodiment of the present invention there is provided use of the *Withania somnifera* extracts comprising about 70-80% withanolides and about 15-25% withanoside for preparation of medicament useful for the treatment of neurodegenerative disorders is selected from a group consisting of Alzheimer's disease, Parkinson's disease and senile dementia.

In another embodiment of the present invention there is provided use of the *Withania somnifera* extracts comprising 75% withanolides and 20% withanoside for preparation of medicament useful for the treatment of neurodegenerative disorders is selected from a group consisting of Alzheimer's disease, Parkinson's disease and senile dementia.

While the invention is described in connection with preferred embodiments, it will be understood that it is not intended to limit the invention to these embodiments. On the contrary, it is intended to cover all alternatives, modifications, and equivalents as may be included within the spirit and scope of the invention as defined by the appended claims.

EXAMPLES

It should be understood that the following examples described herein are for illustrative purposes only and that various modifications or changes in light of the specification will be suggestive to person skilled in the art and are to be included within the spirit and purview of this application and the scope of the appended claims.

Example 1

Isolation of Active Fraction from *Withania somnifera*

The powdered plant material i.e. roots of *Withania somnifera* was obtained from Arya Vaidya Shala, Kottakkal, India. Plant extract was prepared by adding $CHCl_3$/MeOH (1:1) to root powder in a round bottom flask and stirred for 72 hours at room temperature using a mechanical stirrer. The contents were filtered and the solvent was removed from the clear filtrate under reduced pressure using rotavapor at 35-40° C. preferably 37° C. Fresh $CHCl_3$/MeOH (1:1) was added to the extracted plant material and the extraction procedure was repeated four times. All the four extracts were checked on TLC using $CHCl_3$ and $CHCl_3$/MeOH (90:10) solvent systems, to ensure homogeneity with respect to their chemical components. All the four extracts were found to contain similar components and were therefore combined. The solvent was removed from the combined extract using the above-mentioned conditions until frothing started. The traces of solvent left were removed by air-drying at room temperature and the dried extract was labeled as WS-1.

A test sample of WS-1 was checked for its solubility in various solvents starting form non polar to polar viz., petroleum ether, $CHCl_3$, $CH_3COCH_3$ and MeOH. Finally $CHCl_3$/MeOH (90:10), was chosen for further fractionation. Thus, air dried fraction WS-1 was treated with $CHCl_3$/MeOH (90:10) (3×400 ml) to dissolve most of the soluble components, Solvent was removed from it as above and the fraction left was found to be active and labeled as WS-1a (drug). The insoluble part was also dried and labeled as WS-1b. The active fractions (WS-1a) obtained from different batches were also checked on HP-TLC and found to contain similar components in same proportions. The yield of the extract was about 20 gm per kg of the root powder.

Example 2

Transgenic Animals

Animals

The present study used heterozygous B6C3Tg animals of both genders consisting of young (9 months) and old (23 months) mice and age matched non-transgenic littermates. B6C3Tg double transgenic mice express a chimeric mouse/human amyloid precursor protein (Mo/HuAPP695swe) and a mutant human presenilin 1 (PS1-dE9). The Swedish mutations (K595N/M596L) in APP and exon 9 deletion in PS1 elevate the amount of A-beta produced by the transgene by favoring processing through the beta-secretase pathway. Mice were procured from Jackson lab, USA (Borchelt et al., 1996; Jankowsky et al., 2001). The genetic constitution of newborn mice was tracked periodically by genotyping.

The genetic constitutions of newborn mice were tracked periodically by genotyping. Offsprings were genotyped for the presence of transgene by PCR amplification of genomic DNA extracted from tail.

Extract and Feeding Schedule

The plant extract (0.1-1 gm/kg) body weight was suspended in ethanol such that 25 µl could be administered orally as a single dose daily for 30 days. Middle-aged and old mice were fed the plant extract or vehicle (ethanol) orally for a period of one month. The treatment protocol included treatment for 3 days without behavioral assessment followed by treatment and behavioral paradigm for the next 28 days.

Behavioral Paradigm

The mice were trained in a Radial Arm Maze (RAM) consisting of eight identical and equally spaced arms radiating from a central octagonal platform, elevated to a height of 75 cm. RAM is used as a method for assessing spatial and working memory. Behavioral assessment in RAM included checking for correct working memory error (number of reentries into a baited arm), incorrect working memory error (number of reentries into unbaited arm), reference memory error (number of first entries into unbaited arm; maximum of 4 per trial) and time of experiment (time to complete a trail) (Yee et. al 2004).

Behavioral testing was carried out for 28 days and included the following:
(i) 3 days of acclimatization
(ii) 10 days of pre-training
(iii) 15 days of training and recording. The last three days of training also includes video recording.

Example 3

Immunohistochemistry and Staining Protocol

Animals were treated with drug and vehicle for a period of a month and sacrificed at the end. Brains were extracted, cerebral hemispheres were separated and left hemisphere was kept in 4% paraformaldehyde for fixing and left for 24 hours. The brain was then kept in 30% sucrose solution until the brain sank in the solution. It was then sectioned using cryostat at a thickness of 30 µm. Sections were kept floating in PBS solution. Every $10^{th}$ section was mounted on slides.

Silver Staining

Sections were washed thrice in distilled water for three minutes each (washing step) and then dipped in 10% pre-warmed silver nitrate solution for 15 minutes. The washing step was repeated and the washed sections were kept in ammoniacal silver nitrate solution for 30-45 min. The sections were then put into developer solution until color developed. The sections were then kept in 1% ammonia solution to stop the reaction. The washing step was again repeated and the sections were then kept in 5% sodium thiosulfate for 5 mins to remove excess stain (Beech R, Davenport H 1933). The sections were then given a gradient alcohol treatment and xylene treatment for dehydration and then cover-slipped using DPX. Images were taken under microscope and the plaque burden was measured using IM50 software supplied by Leica.

Immunohistochemistry

Sections were washed thrice in distilled water for three minutes each (washing step). The sections were then dipped in sodium citrate buffer and kept in a pressure cooker till the first whistle, for antigen retrieval. Sections were then quenched in 3% $H_2O_2$ made in PBS for 20 mins. The washing step was repeated. Blocking was done using normal goat serum (3-5%), for 1 hr. Sections were then kept in primary antibody solution (1:500) in blocking solution at 4° C. overnight. Washing step was again repeated. The sections were then kept in secondary antibody (1:500) in PBS and kept for 1-2 hr at room temperature. The washing step was repeated. Signal enhancement was done using avidin-biotin complex, commercially available from Vector. Finally color was developed using DAB or NOVA red kit commercially available from Vector. Sections were washed with distilled water to stop the reaction. The sections were then given a gradient alcohol treatment and xylene treatment for dehydration in case of DAB whereas in case of Nova red only xylene was used for dehydration and then cover-slipped using DPX. Images were taken under microscope and the plaque burden measured using IM50 software.

Example 4

ELISA Protocol

Tissue Preparation

Animals were treated with drug and vehicle for a period of a month and sacrificed 24 hr after the last dose. Brains were dissected, cerebral hemispheres were separated and right hemisphere was dissected into five major parts: Frontal cortex, Rest of the cortex, Hippocampus, Cerebellum, Rest of the brain. The tissues were snap frozen using liquid nitrogen and then homogenized and centrifuged for separation as whole homogenate, post nuclear supernatant and cytosol fractions. The whole homogenate was treated with guanidine-HCl (5 M). Elisa was done for beta amyloid 1-42 and 1-40 using antibodies 12F4 and 11A50-B10 respectively (Signet covance).

Plate Preparation

ELISA plates were coated with capture antibody (12F4 or 11A50-B10, Signet covance) with concentration 1.5 µg/ml using coating buffer (0.05 M $NaHCO_3$, 0.05 M $Na_2CO_3$ in distilled water, pH 9.4) for overnight at 4° C. Wells were washed using wash buffer (0.15 M NaCl, 0.1% Tween), for 15-30 s and aspirated followed by blocking with 300 µL of blocking solution (0.14 M NaCl, 8 mM $Na_2HPO_4.2H_2O$, 1.5 mM $KH_2PO_4$, 2.6 mM KCl, 0.5% bovine serum albumin, in water, pH 7.4).

Plates were covered and incubated for 1 to 2 hr at room temperature. Blocking solution was aspirated from the wells. Standards and samples were diluted in assay buffer (0.14 M NaCl, 8 mM $Na_2HPO_4.2H_2O$, 1.5 mM $KH_2PO_4$, 2.6 mM KCl, 0.5% bovine serum albumin, 0.1% Tween 20, in water, pH 7.4) and added to coated plates and incubated for 2 hr. Solution was aspirated and wells were washed four times (30 s each). Detection antibody (polyclonal beta amyloid H-43, Santa Cruz Inc.) was diluted to 0.5 µg/ml and added into wells and incubated for one hr followed by washing step. Biotinylated secondary antibody was diluted in assay buffer and added to wells and incubated for 1 hr followed by washing. Streptavidin HRP was diluted and added to wells and incubated for 30 minutes. Colour was developed using TMB kit and $1NH_2SO_4$ was added to stop the reaction. OD was taken at 450 nm using ELISA reader from Biorad. For analysis standard curve was plotted and curve fitting was done using non-linear regression of order three and concentration of samples was calculated.

Example 5

Experiment Performed with 9 Months Old B6C3Tg Mice Using Plant Extract Dose=1 g/kg of Body Weight Behavior Transgenic mice 9-10 months old (mutated for the gene APP and PS1) were treated with the plant extract (PE) and vehicle for one month with a dose of 1 gm/kg body weight. Animals were trained and tested for their spatial learning and memory on the radial arm maze. Transgenic mice treated with PE showed reduction in memory errors (FIG. 1).

Staining

These mice were sacrificed and their brains were processed for staining and biochemical assays. The frozen sections were stained using Silver staining, beta amyloid immuno-histochemistry (IHC) and Ubiquitin IHC.

Figure 2:
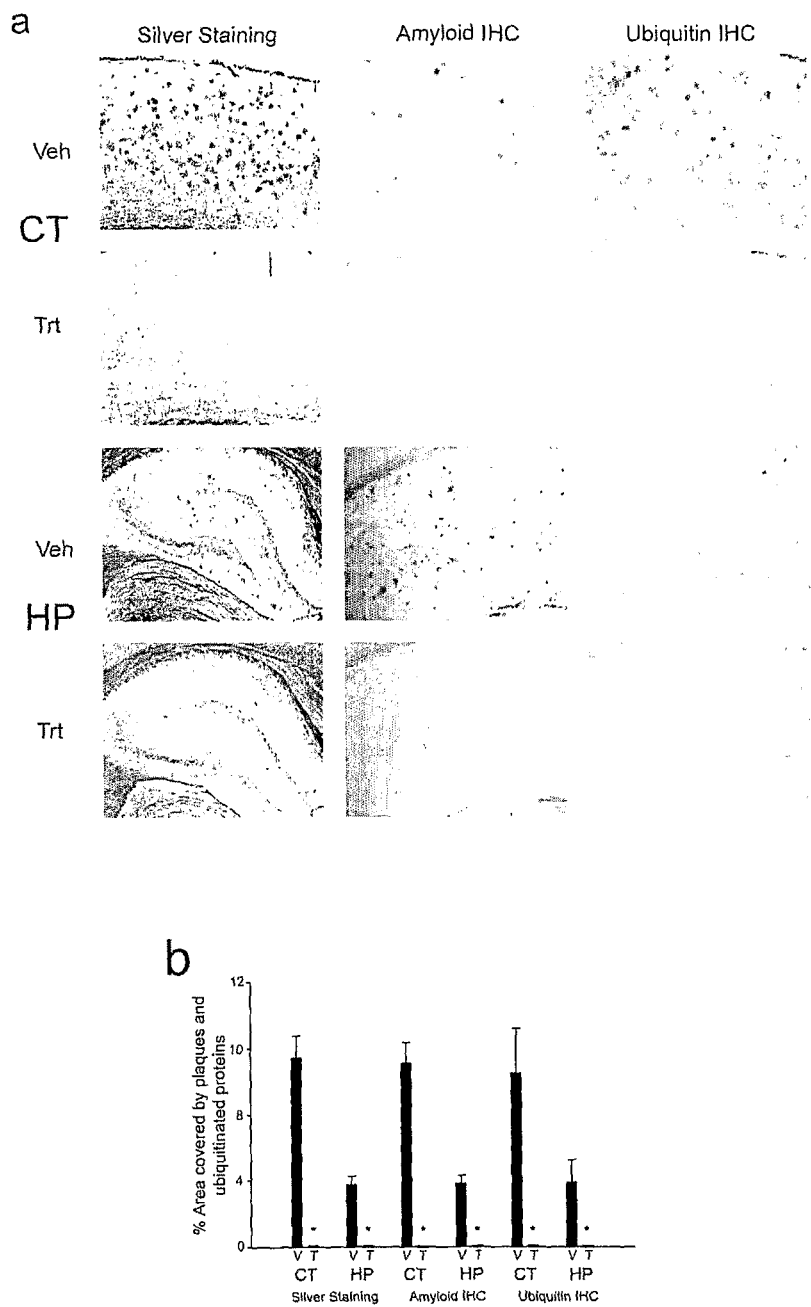
FIG. 2 shows Tg mice (9 months old) on treatment with plant extract (dose: 1 gm/kg body weight) showed complete removal of plaques and ubiquitinated protein aggregates.

Treatment with plant extract resulted in complete removal of plaques as compared to the vehicle treated mice. Stereology was done and the percentage area of the cortex or hippocampus covered by plaques was calculated. (FIG. 2)

Amyloid Load Using ELISA

ELISA was performed to quantify different forms of Aβ. The beta amyloid loads of Aβ 1-40, Aβ 1-42 in cortex, hippocampus and serum of the same mice were measured using ELISA and it was found that there was a significant reduction in Aβ 1-40 and Aβ 1-42 in the brain as well as in the serum (FIG. 3-4).

Example 6

Experiment Performed with 9 Months Old B6C3Tg Mice Using Plant Extract Dose 0.1 g/Kg & 0.5 g/Kg of Body Weight The above experiments were repeated using two different dosages 0.1 g/kg and 0.5 g/kg body weight. The results are as follows Staining Even the lower doses of the plant extract led to significant reduction in plaque load (FIG. 5).

Amyloid Load Using ELISA

We observed significant reduction in beta amyloid of Aβ 42 and Aβ 40 load with the dose of 0.5 g/kg body weight (FIG. 6).

Example 7

Experiment Performed with 23 Months Old B6C3Tg Using Plant Extract Dose=1 g/kg of Body Weight Similar experiments were carried out for 23 months old transgenic mice.

Behavior

Older Tg mice treated with plant extract performed better on radial arm maze task as compared to vehicle treated Tg mice. There was a significant reduction in memory errors as compared to vehicle treated mice. (FIG. 7)

Staining

There was a significant reduction in plaque load in plant extract treated Tg animals as compared to vehicle treated Tg animals (FIG. 8)

Amyloid Load

The beta amyloid load of Aβ 1-40 and Aβ 1-42 in cortex, hippocampus and serum of the same mice were measured using ELISA and it was found that there was a significant reduction in Aβ 1-40, Aβ 1-42 in brain as well as in serum (FIG. 9).

We claim:

1. A *Withania somnifera* extract comprising about 70-80% withanolides and about 15-25% withanoside, wherein, the extract is prepared by a process comprising
   providing *Withania somnifera* root powder;
   extracting said root powder with a 1:1 ratio of methanol:chloroform mixture at room temperature for about 60-75 hours to obtain a root extract;
   removing the methanol:chloroform from the root extract to obtain a dry root extract;
   treating the dry root extract with a 10% methanol-chloroform mixture to obtain the *Withania somnifera* plant extract;
   wherein the extract is free of withaferin.

2. The *Withania somnifera* extract as claimed in claim 1, wherein the extract comprises 75% withanolides and 20% withanoside.

3. The *Withania somnifera* extract as claimed in claim 1, wherein the extract is useful for the treatment of neurodegenerative disorders selected from a group consisting of Alzheimer's disease, Parkinson's disease and senile dementia.

4. The *Withania somnifera* extract as claimed in claim 1, wherein the extract is in the form of powder, liquid, capsules or tablets.

5. The *Withania somnifera* extract as claimed in claim 1, wherein the extract is useful for treatment of Alzheimer's disease.

6. The *Withania somnifera* extract as claimed in claim 4, wherein effective dosage of the extract for the treatment of Alzheimer's disease is in the range of 0.5 g/day/kg body weight to 1 g/day/kg body weight.

7. A pharmaceutical composition comprising the *Withania somnifera* extract as claimed in claim 1 and a pharmaceutical acceptable carrier.

8. A nutritional composition comprising the *Withania somnifera* extract as claimed in claim 1.

9. An herbal composition comprising the *Withania somnifera* extract as claimed in claim 1.

* * * * *